United States Patent [19]

McIlroy et al.

[11] 4,439,679
[45] Mar. 27, 1984

[54] TRANSCUTANEOUS GAS TENSION MEASUREMENT USING A DUAL SAMPLING CHAMBER AND GAS ANALYSIS SYSTEM

[75] Inventors: Malcolm B. McIlroy, Belvedere; Ralph C. Targett, El Cerrito, both of Calif.

[73] Assignee: The Regents of the University of California, Berkeley, Calif.

[21] Appl. No.: 252,886

[22] Filed: Apr. 10, 1981

[51] Int. Cl.³ .............................................. B01D 59/44
[52] U.S. Cl. .................................... 250/282; 250/288
[58] Field of Search ............... 250/281, 282, 283, 288; 128/632, 635

[56] References Cited

U.S. PATENT DOCUMENTS

| | | | |
|---|---|---|---|
| 3,649,199 | 3/1972 | Littlejohn | 23/230 B |
| 3,659,586 | 5/1972 | Johns et al. | 128/2 E |
| 3,795,239 | 3/1974 | Eberhard et al. | 128/2 E |
| 4,005,700 | 2/1977 | Parker | 128/2 E |
| 4,016,863 | 4/1977 | Brantigan | 128/2 G |
| 4,220,158 | 9/1980 | Delpy et al. | 128/632 |

OTHER PUBLICATIONS

McIlroy, M. B. et al., "Microcomputer Analysis of Transcutaneous Gas Tension Masurement . . . ," 15th Annual AAMI Meeting, Apr. 13-17, 1980.
Hansen, T. N. et al., J. Appl. Physiol. 49 (3): 438-443, (1980).
Delpy, D. et al., Lancet, May 3, 1975, p. 1016.

Primary Examiner—Bruce C. Anderson
Attorney, Agent, or Firm—Flehr, Hohbach, Test, Albritton & Herbert

[57] ABSTRACT

A device for the measurement of the tension of blood gases and resistance of the skin to the flow of said gases comprising a body having a gas permeable boundary comprising two gas permeable membranes for placement on the skin of the subject, two gas collection chambers in the body connected to a gas analysis system, a heating device to heat the skin area under the boundary and control means operable to control said heating device.

8 Claims, 4 Drawing Figures

TRANSCUTANEOUS GAS TENSION MEASUREMENT USING A DUAL SAMPLING CHAMBER AND GAS ANALYSIS SYSTEM

BACKGROUND OF THE INVENTION

The present invention relates to a device for the measurement of the tension of blood gases and the resistance of the skin to the flow of such gases.

The invention described herein was made in the course of work under a grant or award from the Department of Health and Human Services.

Examples of single chamber transcutaneous probes are known in the art, such as shown in U.S. Pat. Nos. 4,005,700 and 4,220,158. Such probes may comprise a hollow body having a boundary wall which is placed on the skin, a single internal chamber in which gas diffusing through the skin contacted by the boundary wall can be collected, heating means operable to heat the area of skin and a single outlet from the collecting chamber through which the collected gas may be led away to an analysis instrument. Typically, the boundary wall may comprise a membrane of gas permeable plastic supported by a porous supporting member. The method employing such devices relies upon the diffusion of the blood gases from the capillary circulation beneath the skin to the surface of the skin. The measurement of the partial pressure of gases eliminated from the skin reflects its capillary gas tension. However, in order to more accurately reflect arterial gas tensions, the surface of the skin is heated to about 43° C. so that blood flow to the capillaries is increased to such an extent that the gas tensions measured at the skin approximate arterial gas tensions. Such devices known in the prior art may be used for the measurement of the arterial blood content of certain gases, such as oxygen and carbon dioxide, without the need for arterial catheterization. Instruments for monitoring arterial oxygen and carbon dioxide are useful, for example, in neonatal care and during intensive medical care of adults.

One disadvantage of the prior art devices is that they cannot measure the resistance which the skin itself offers to the flow of gas from the blood through the tissues. Therefore, under any estimation of arterial blood gas tension using devices of the prior art, only changes in such blood gas tensions can be measured since it must be assumed that the skin resistance to gas flow remains constant. Therefore, absolute arterial blood gas tensions cannot be measured by devices known in the prior art since there was no way to measure skin resistance. Furthermore, the devices of the prior art may only be used under conditions in which it would be reasonable to assume that the skin resistance remains constant. Therefore, the measurements taken would only have meaning on a particular patient, taken on a particular area of skin, under conditions of temperature humidity, etc., for which it would be reasonable to assume that the skin resistance does not significantly change while measurements were being taken. However, the devices of the prior art may not be used when it is needed to compare arterial gas tensions between different patients or between different areas of skin on the same patient, since skin resistance varies in different parts of the body and from patient to patient. Also, under certain conditions, it has been found that skin resistance to diffusion of particular gases is time dependent. Therefore, in such cases the monitoring of a particular gas being eliminated from the skin tissues using devices of the prior art would not accurately reflect instantaneous arterial gas tensions.

SUMMARY OF THE INVENTION

According to the present invention, there is provided a device for the measurement of the partial pressure of gases eliminated from the blood stream of animals through the skin and the resistance of the skin of said animals to the flow of said gases, said device comprising a body defining two gas collecting chambers, said body having one wall which can be placed in contact with the skin of an animal comprising a wall portion of each of said chambers wherein each wall portion is defined by a gas permeable membrane, said device further comprising heating means operable to heat said body in the area of skin in contact therewith, an outlet from each of said chambers through which gas collected therein is led to a gas analysis system, valve means to control the flow of gases through at least one of said outlets, and control means responsive to the temperature of the area of skin in contact with said wall and operable to control said heating means. The gas analysis system comprises a gas analysis instrument, such as a mass spectrometer, and an integrated calculating system which uses the output generated by the gas analysis instrument to calculate the capillary gas tension of each gas sensed by the gas analysis instrument and the resistance of the skin to the flow of such gas. An application of the instant invention is to produce measurements of the capillary gas tension of metabolized gases, such as oxygen and carbon dioxide, which are more accurate than those which may be made by the single chamber sampling devices of the prior art. In addition, the instant invention may be used to accurately measure the skin resistance to the flow of gases, a measurement which may not be made by the single chamber devices known in the art.

An additional application of the instant invention to measure the capillary gas tension and skin resistance to non-metabolized gases, such as nitrogen and helium. This is a particular advantage of the instant invention since the elimination through the skin of such non-metabolized gases, in particular nitrogen, occurs relatively slowly and it is possible that the skin resistance to nitrogen changes during the elimination process. The invention therefore would have practical application in the monitoring of nitrogen elimination from divers in decompression chambers to determine when it was safe for the divers to return to sea level atmosphere. Furthermore, there may be variations in the tolerance of different persons to high pressures, perhaps related to their body composition, and the instant invention may be used to test subjects to discover whether they were suitable for training for diving operations.

The measurement of capillary gas tension of non-metabolized gases is not limited to nitrogen. For example, the instant invention may also be used to monitor the tissue tensions of anesthetic gases during surgery.

DESCRIPTION OF THE INVENTION

The invention will be now more particularly described by way of example with reference to the accompanying drawings.

Figure 1:
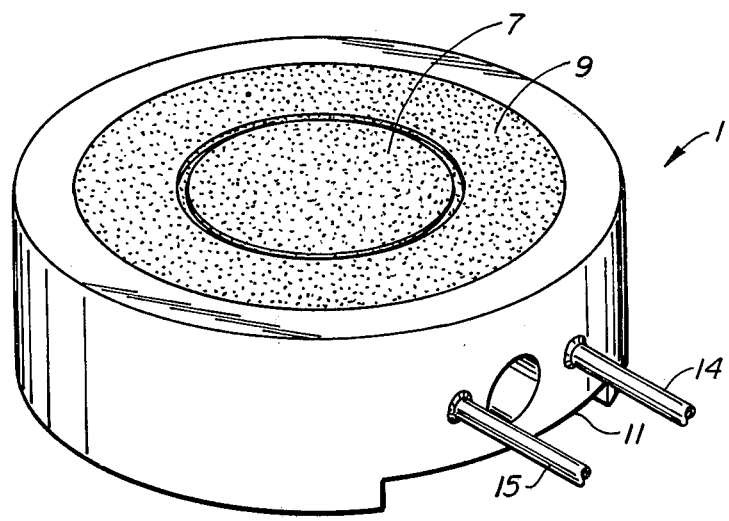
FIG. 1 is a perspective view of one embodiment of the transcutaneous probe in accordance with the invention.

Referring to FIG. 1, the illustrated transcutaneous probe comprises a body 1 defining two gas collecting chambers 2 and 3.

Figure 2:
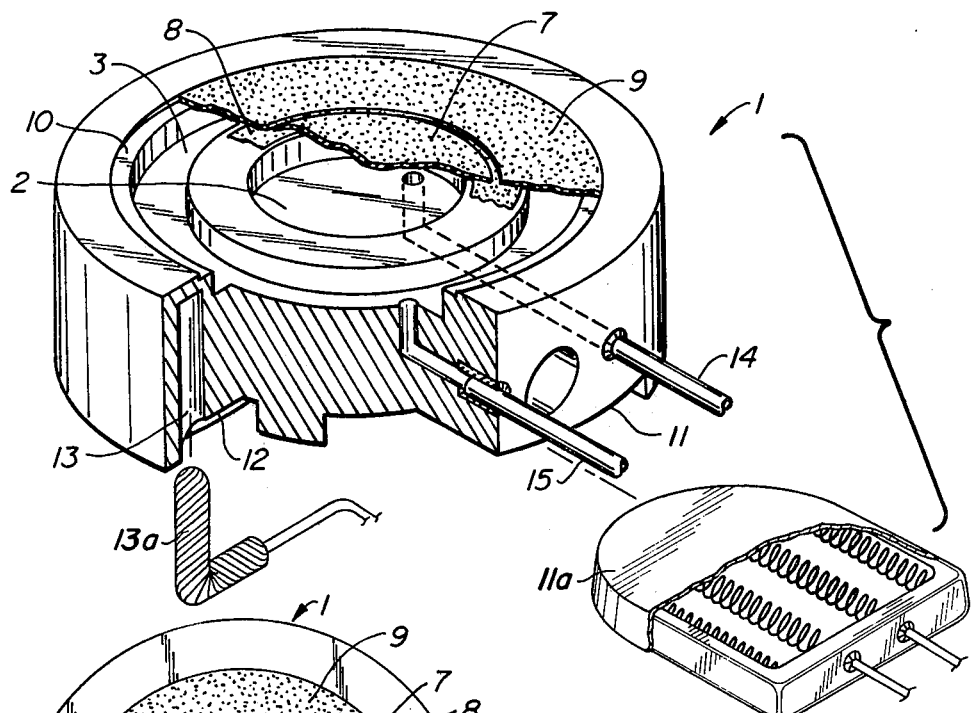
FIG. 2 is a partially sectioned perspective view of the transcutaneous probe shown in FIG. 1.

Referring to FIG. 2, the upper wall of said inner chamber 2 comprises a gas permeable film 7. The upper wall of the outer chamber 3 is co-planar with the upper wall of the inner chamber and comprises a gas permeable film 9. Films 7 and 9 are fixed to body 1 by adhesive material 8. Adhesive material, not shown, is also present on surface 10. The coplanarity of films 7 and 9 allows the upper wall of body 1 to be placed against the skin of a subject thereby allowing gases expelled from the skin to diffuse through said films 7 and 9 into the collecting chambers 2 and 3.

Heating means 11A may be fixed onto body 1 in the laterally slotted area 11 located on the lower surface of said body. The L-shaped aperture defined by lateral slot 12 and vertical aperture 13 may accommodate heating control means 13A which is responsive to the temperature within said body 1 which is in contact with the skin of the subject. Said heating control means is operable to maintain a constant temperature or temperature range within said body 1.

Figure 3:
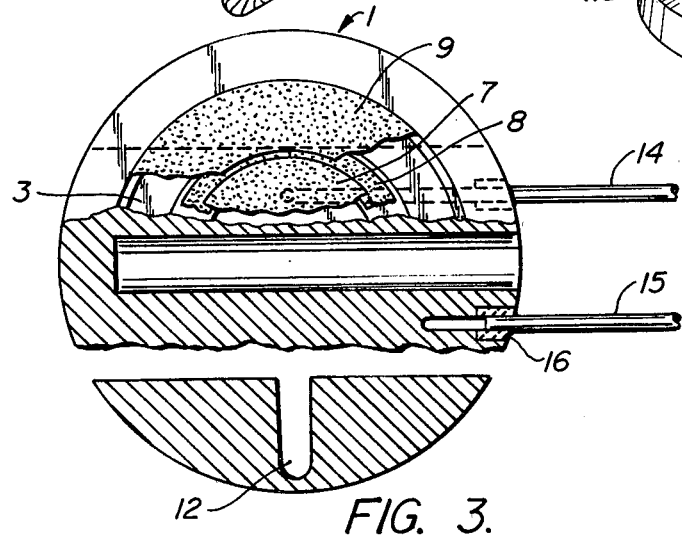
FIG. 3 is a partially sectioned plan view of the transcutaneous probe shown in FIG. 2.

Referring to FIG. 3, lateral slot 12 is more clearly shown. The gases from chambers 2 and 3 are led through outlets comprising tubes 14 and 15, respectively, which may be firmly fixed to body 1 by solder, glue, weld or other similar bonding material illustrated by 16.

Figure 4:
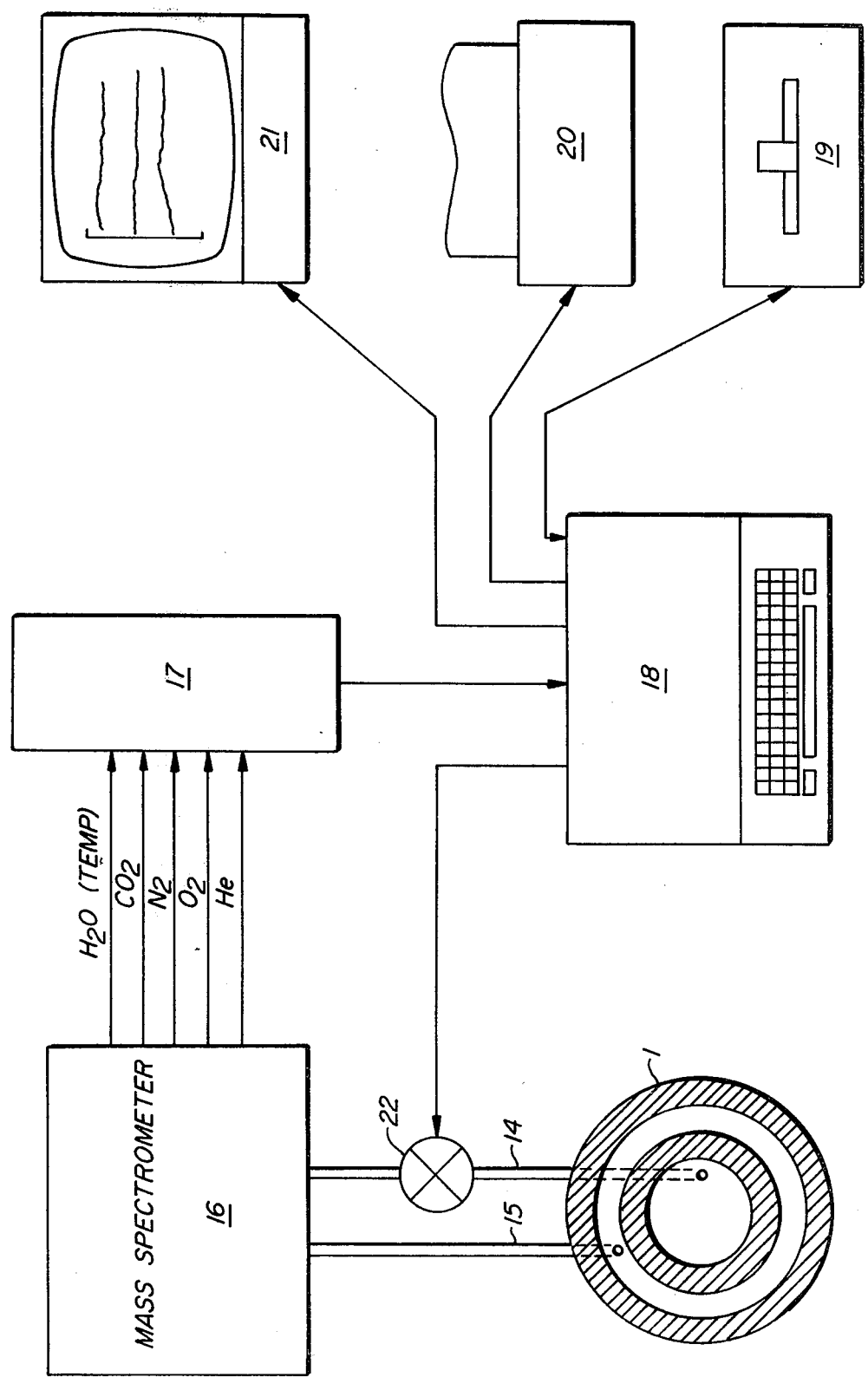
FIG. 4 is a block diagram of the transcutaneous probe and gas analysis system according to the instant inventor.

Referring to FIG. 4, the gases are led through outlets 14 and 15 into gas analysis instrument 16. As illustrated, outlet 14 is provided with valve means 22 to control the flow of gases through said outlet. Gas analysis instrument 16 is integrated with input converting instrument 17 which converts the output from instrument 16 to an input form readable by computer 18. As illustrated, instrument 16 measures various gas partial pressures such as carbon dioxide, nitrogen, oxygen and helium. Preferably instrument 16 is a mass spectometer which may be calibrated to measure any vapor or gas. The temperature of the gases is indirectly measured by measuring the partial pressure of water vapor, which is directly correlated to temperature. Computer 18 is integrated with programming means 19, which provides the program for calculations to be performed by computer 18. Preferably, computer 18 is a microcomputer and programming means 19 is a disc drive. The output from computer 18 comprising capillary gas tensions and skin resistance may be printed on printer 20 or viewed on video monitor 21.

In the operation of the invention body 1 is placed in contact with the skin of a subject so that films 7 and 9 are in intimate contact therewith. Body 1 may be heated by heating means so that the area of skin in contact with said body is warmed to a temperature from 43° C. to 45° C. Valve means 22 is opened and the gases collected in chambers 2 and 3 which have diffused through the skin are led through conduits 14 and 15 into gas analysis instrument 16, which may preferably be a mass spectrometer. This gives the partial pressure of gas flow through the resistances consisting of film 7, film 9 and the subject's skin. A second measurement is then taken by closing valve 22 so that the gas flowing into gas analysis instrument 16 originates from chamber 3 alone. From this measurement is determined the partial pressure for the measured gas as it flows through the resistance of the subject's skin and film 7. Since the resistance of each membrane 7 and 9 is known, together with the gas pressures from chamber 3 alone and from combined chambers 2 and 3, it is possible to solve the two simultaneous equations having the two unknown values: (1) capillary gas tension of the measured gas through the subject skin and (2) the resistance of the skin to said gas flow. The mathematical principles involved in calculating the resistance of the skin to any gas according to such equations are described by Eberhard and Severinghaus in *Acta Anesth. Scand*, Supp. 68, 1–3, 1978, the disclosure of which is incorporated herein by reference. The multiple computations involved in using these equations to calculate the capillary gas tension and skin resistance for several gases from repeated samples of gas from the skin may be performed by the integrated system comprising convertor 17, computer 18 and programmer 19.

It is preferred that one of the films 7 and 9 have a resistance to the flow of gases approximately the same as that of human skin, while the other film have a resistance to the flow of gases greater than that of human skin. As an example, one of the films may be made of polytetrafluoroethylene, such as Teflon ®, having a thickness of approximately 2 mil. and the other film may be made of biaxially oriented polypropylene having a thickness of about 0.85 mil.

The body of the device of the invention may comprise any gas-impermeable material having structural integrity and being heat resistant up to about 60° C. Preferably, such material may be heat conductive. The preferred materials are brass and stainless steel.

The gas analysis instrument is preferably a mass spectrometer which typically contains a vacuum ionization chamber. Since the gas sampling chambers of the instant invention are vacuum tight, the pressure drop from atmospheric pressure to the low pressure within the mass spectrometer takes place across the films covering each part of the sampling chambers. The films may be attached at their perimeters to the sampling chambers by double-sided adhesive material.

The temperature within the body 1 may be controlled to within about 0.2° C. by commercially available servoelectric systems. The gas tension of membranes 7 and 9 to the particular gases which are to be analyzed may be calibrated by exposing the chambers to gas mixtures of known composition in a calibration chamber heated to the same temperature as the sampling chamber and by bubbling the sample gas through water in the chamber.

In the preferred embodiment of the invention the outputs from the mass spectrometer consist of voltages from electrometers monitoring the collection cups for each gas in the ionization chamber. These outputs from the mass spectrometer form the inputs into converting instrument 17. In the initial calibration procedure the voltages for each gas at specific temperatures are recorded in the computer member while calibrating gas flows of known partial pressures through films 7 and 9. These calibration values for films 7 and 9 to known gas pressures may then be used to solve the simultaneous equations for the gas tension of each gas and skin resistance when the sampling chamber is applied to the heated skin of the subject under test.

While we have described particular embodiments of our invention for purposes of illustration, it will be understood that the invention is not to be taken as limited except by the scope of the appended claims.

What is claimed is:

1. A device for the measurement of the tensions of gases in the blood stream of an animal, including man, and for the measurement of the resistance of the skin of said animal to the flow of said gases, said device comprising a body defining two gas collecting chambers, said body having one wall which can be placed in contact with the skin of said animal comprising a wall portion of each of said chambers wherein each wall portion is defined by a gas-permeable membrane said membranes being coplanar, said device further comprising heating means operable to heat said body in the area of skin in contact therewith, an outlet from each of said chambers through which gases collected therein are led to a gas analysis system, valve means to control the flow of gases through at least one of said outlets, and control means responsive to the temperature of the area of skin in contact with said body operable to control said heating means.

2. A device according to claim 1 wherein one of said gas-permeable membranes is characterized by having substantially the same resistance to the flow of gases as human skin and the other gas permeable membrane film is characterized by having a greater resistance to the flow of gases than the first membrane.

3. A device according to claim 2 wherein said gas analysis system comprises a gas analysis instrument and a computer integrated therewith.

4. A device according to claim 3 wherein said gas analysis instrument is a mass spectrometer.

5. A device according to claim 2 wherein said membrane having substantially the same resistance to the flow of gases as human skin comprises biaxially oriented by polypropylene and said other gas permeable plastic film comprises polytetrafluoroethylene.

6. A method of simultaneously measuring the tensions of gases in the blood stream of an animal, including man, and the resistance of the skin of said animal to the flow of said gases comprising the steps of contacting an area of the skin of said animal with the gas permeable boundary walls of two collecting chambers, heating the area of skin defined by said boundary walls, and continuously monitoring the temperature of said area of skin, collecting in said collecting chambers gases which have diffused through said area of skin and passing said gases to a gas analysis instrument, measuring the proportions and changes in proportions of gaseous constituents of the gases flowing from both collecting chambers, halting the flow of gases from one of said chambers to said instrument, measuring the proportions and changes in proportions of the gaseous constituents of the gases flowing from the single collecting chamber, and determining the resistance of the skin of the subject to the flow of said gaseous constituents, and the tensions of said gaseous constituents in the bloodstream of said animal.

7. The method according to claim 6 wherein one of said gas-permeable boundary walls is characterized by having substantially the same resistance to the flow of gases as human skin and the other gas-permeable boundary wall is characterized by having a greater resistance to the flow of gases than the first gas-permeable boundary wall.

8. The method according to claim 7 wherein said gas-permeable boundary wall is characterized as having substantially the same resistance to the flow of gases as human skin comprises biaxially oriented polypropylene and said other gas-permeable boundary wall comprises polytetrafluoroethylene.

* * * * *